(12) United States Patent
Chowaniec et al.

(10) Patent No.: US 11,877,744 B2
(45) Date of Patent: Jan. 23, 2024

(54) LOW-COST POWERED STAPLER WITH END STOP SELECTION

(71) Applicant: Covidien LP, Mansfield, MA (US)

(72) Inventors: David M. Chowaniec, Rocky Hill, CT (US); Xingrui Chen, Glastonbury, CT (US); Drew R. Seils, Guilford, CT (US); Thomas S. Wingardner, North Haven, CT (US); Andriy Buyda, East Haven, CT (US); Jennifer Mccabe, Middletown, CT (US)

(73) Assignee: COVIDIEN LP, Mansfield, MA (US)

( * ) Notice: Subject to any disclaimer, the term of this patent is extended or adjusted under 35 U.S.C. 154(b) by 151 days.

(21) Appl. No.: 17/395,744

(22) Filed: Aug. 6, 2021

(65) Prior Publication Data

US 2022/0047262 A1 Feb. 17, 2022

Related U.S. Application Data

(60) Provisional application No. 63/065,601, filed on Aug. 14, 2020.

(51) Int. Cl.
*A61B 17/072* (2006.01)
*A61B 90/00* (2016.01)
(Continued)

(52) U.S. Cl.
CPC ............ *A61B 17/072* (2013.01); *A61B 90/03* (2016.02); *A61B 90/30* (2016.02);
(Continued)

(58) Field of Classification Search
CPC .......... A61B 90/03; A61B 2017/00367; A61B 2017/07257; A61B 2017/07271
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| (Continued) | | |

FOREIGN PATENT DOCUMENTS

| | | |
|---|---|---|
| CA | 908529 A | 8/1972 |
| CA | 2805365 A1 | 8/2013 |
| (Continued) | | |

OTHER PUBLICATIONS

Extended European Search Report from Appl. No. 14181908.6 dated May 26, 2015.
(Continued)

*Primary Examiner* — Robert F Long
*Assistant Examiner* — Xavier A Madison
(74) *Attorney, Agent, or Firm* — Carter, DeLuca & Farrell LLP

(57) ABSTRACT

A surgical stapler includes a loading unit having a staple cartridge having a cartridge distance and a plurality of staples and an anvil to form the plurality of staples upon firing. The surgical stapler also includes a shaft assembly coupled to the load unit. The shaft assembly includes a drive shaft longitudinally movable within the shaft assembly and configured to actuate the loading unit. The surgical stapler further includes a handle assembly having a power source and a motor coupled to the power source and configured to move the drive shaft longitudinally. The handle assembly also includes a distance setting interface including a plurality of switches each of which corresponds to a travel distance that the motor moves the drive shaft, the travel distance corresponding to the cartridge distance.

18 Claims, 5 Drawing Sheets

(51) Int. Cl.
*A61B 90/30* (2016.01)
*A61B 17/00* (2006.01)
(52) U.S. Cl.
CPC ............ *A61B 2017/00367* (2013.01); *A61B 2017/07257* (2013.01); *A61B 2017/07271* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,017,354 A | 1/2000 | Culp et al. |
| 6,024,748 A | 2/2000 | Manzo et al. |
| 6,025,683 A | 2/2000 | Philipp |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,090,123 A | 7/2000 | Culp et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |

(56) References Cited

U.S. PATENT DOCUMENTS

| | | |
|---|---|---|
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,237,604 B1 | 5/2001 | Burnside et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Teck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,565 B1 | 2/2003 | Whitman et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,556,778 B2 | 4/2003 | Zhang et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,611,793 B1 | 8/2003 | Burnside et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,940,255 B2 | 9/2005 | Loch |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,126,310 B1 | 10/2006 | Barron |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,193,519 B2 | 3/2007 | Root et al. |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,117 B2 | 10/2007 | Krueger et al. |
| 7,285,125 B2 | 10/2007 | Viola |
| 7,285,177 B2 | 10/2007 | Bushoff et al. |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,362,062 B2 | 4/2008 | Schneider et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,400,107 B2 | 7/2008 | Schneider et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,514,890 B2 | 4/2009 | Schneider et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,638,958 B2 | 12/2009 | Philipp et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |

(56) References Cited

U.S. PATENT DOCUMENTS

| | | |
|---|---|---|
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,738,971 B2 | 6/2010 | Swayze et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,784,663 B2 | 8/2010 | Shelton, IV |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 7,998,157 B2 | 8/2011 | Culp et al. |
| 8,002,795 B2 | 8/2011 | Beetel |
| 8,006,701 B2 | 8/2011 | Bilotti et al. |
| 8,006,889 B2 | 8/2011 | Adams et al. |
| 3,011,554 A1 | 9/2011 | Milliman |
| 8,011,551 B2 | 9/2011 | Marczyk et al. |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,154,239 B2 | 4/2012 | Katsuki et al. |
| 8,157,153 B2 | 4/2012 | Shelton, IV et al. |
| 8,161,977 B2 | 4/2012 | Shelton, IV et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,210,411 B2 | 7/2012 | Yates et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,375,808 B2 | 2/2013 | Blumenkranz et al. |
| 8,399,822 B2 | 3/2013 | Al-Ali |
| 8,400,108 B2 | 3/2013 | Powell et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,473,502 B2 | 6/2013 | Ledford et al. |
| 8,485,414 B2 | 7/2013 | Criscuolo et al. |
| 8,490,853 B2 | 7/2013 | Criscuolo et al. |
| 8,500,769 B2 | 8/2013 | Deng |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,657,174 B2 | 2/2014 | Yates et al. |
| 8,662,370 B2 | 3/2014 | Takei |
| 8,663,258 B2 | 3/2014 | Bettuchi et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,708,213 B2 | 4/2014 | Shelton, IV et al. |
| 8,733,611 B2 | 5/2014 | Milliman |
| 8,746,532 B2 | 6/2014 | Nalagatla et al. |
| 8,806,973 B2 | 8/2014 | Ross et al. |
| 8,808,311 B2 | 8/2014 | Heinrich et al. |
| 8,893,946 B2 | 11/2014 | Boudreaux et al. |
| 8,959,617 B2 | 2/2015 | Newlin et al. |
| 8,989,903 B2 | 3/2015 | Weir et al. |
| 9,017,851 B2 | 4/2015 | Felder et al. |
| 9,084,601 B2 | 7/2015 | Moore et al. |

(56) References Cited

U.S. PATENT DOCUMENTS

| | | |
|---|---|---|
| 9,089,338 B2 | 7/2015 | Smith et al. |
| 9,095,339 B2 | 8/2015 | Moore et al. |
| 9,113,874 B2 | 8/2015 | Shelton, IV et al. |
| 9,142,992 B2 | 9/2015 | Malackowski et al. |
| 9,226,750 B2 | 1/2016 | Weir et al. |
| 9,326,769 B2 | 5/2016 | Shelton, IV et al. |
| 9,326,770 B2 | 5/2016 | Shelton, IV et al. |
| 9,364,249 B2 | 6/2016 | Kimball et al. |
| 9,393,017 B2 | 7/2016 | Flanagan et al. |
| 9,398,911 B2 | 7/2016 | Auld |
| 9,439,651 B2 | 9/2016 | Smith et al. |
| 9,498,219 B2 | 11/2016 | Moore et al. |
| 10,271,851 B2 | 4/2019 | Shelton, IV et al. |
| 10,292,704 B2 | 5/2019 | Harris et al. |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0102472 A1 | 5/2007 | Shelton |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0257636 A1 | 10/2011 | Whitman et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0374371 A1 | 12/2015 | Richard et al. |
| 2016/0095585 A1 | 4/2016 | Zergiebel et al. |
| 2016/0106406 A1 | 4/2016 | Cabrera |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0249945 A1 | 9/2016 | Shelton, IV et al. |
| 2016/0302792 A1 | 10/2016 | Motai |
| 2016/0310134 A1 | 10/2016 | Contini et al. |
| 2017/0172572 A1* | 6/2017 | Collings ............... A61B 17/072 |
| 2022/0031321 A1* | 2/2022 | Sun ................... A61B 17/07207 |

FOREIGN PATENT DOCUMENTS

| | | |
|---|---|---|
| CN | 103 622 727 A | 3/2014 |
| DE | 1057729 B | 5/1959 |
| DE | 3301713 A1 | 7/1984 |
| EP | 0173451 A1 | 3/1986 |
| EP | 0152382 A2 | 8/1986 |
| EP | 0190022 A2 | 8/1986 |
| EP | 0282157 A1 | 9/1988 |
| EP | 0503689 A2 | 2/1992 |
| EP | 1354560 A2 | 10/2003 |
| EP | 2138118 A2 | 12/2009 |
| EP | 2165664 A2 | 3/2010 |
| EP | 2168510 A1 | 3/2010 |
| EP | 2238926 A2 | 10/2010 |
| EP | 2524656 A2 | 11/2012 |
| EP | 2684529 A2 | 1/2014 |
| EP | 2954854 A2 | 12/2015 |
| EP | 3011915 A2 | 4/2016 |
| EP | 3064153 A2 | 9/2016 |
| EP | 3078335 A1 | 10/2016 |
| EP | 3103402 A1 | 12/2016 |
| EP | 3165180 A2 | 5/2017 |
| EP | 3175800 A1 | 6/2017 |
| EP | 3184056 A2 | 6/2017 |
| EP | 3231374 A1 | 10/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

(56) References Cited

FOREIGN PATENT DOCUMENTS

| WO | 2016171947 A1 | 10/2016 |
| WO | 2018234887 A1 | 12/2018 |
| WO | 2020077531 A1 | 4/2020 |

OTHER PUBLICATIONS

European Examination Report from Appl. No. 14181908.6 dated May 3, 2016.
Extended European Search Report dated Nov. 6, 2018 issued in corresponding EP Appln. No. EP18176772.4.
European Examination Report dated Oct. 4, 2019 issued in corresponding EP Appln. No. 18176772.4.
Partial European Search Report dated May 8, 2020 issued in corresponding EP Appln. No. 20154026.7.
Extended European Search Report dated May 8, 2020 issued in corresponding EP Appln. No. 20154027.5.
European Examination Report dated Apr. 22, 2020 issued in corresponding EP Appln. No. 18176772.4.
Extended European Search Report dated Jul. 29, 2020 issued in corresponding EP Appln. No. 20154026.7.
Extended European Search Report dated Oct. 31, 2018 issued in corresponding EP Appln. No. 18176776.5.
European Examination Report dated Oct. 23, 2019 issued as EP Application No. 18176776.5.
Extended European Search Report dated Jan. 10, 2022 issued in corresponding EP Appln. No. 21190874.4.

* cited by examiner

LOW-COST POWERED STAPLER WITH END STOP SELECTION

CROSS-REFERENCE TO RELATED APPLICATIONS

The present application claims the benefit of and priority to U.S. Provisional Patent Application No. 63/065,601 which was filed on Aug. 14, 2020. The entire contents of the foregoing applications incorporated by reference herein.

BACKGROUND

Technical Description

The present disclosure relates to powered surgical staplers. More specifically, the present disclosure relates to electromechanical, hand-held surgical staplers configured for use with removable disposable or reusable loading units of varying length having user-selectable distance setting.

Background of Related Art

Powered surgical staplers utilize one or more motors to actuate various mechanical end effectors having an anvil and a staple cartridge. Stapling end effectors may include reusable loading units and/or single use loading units having staples of various sizes and arranged in one or more configurations (e.g., multiple rows).

The loading units have an end stop, which is an indication that all staples have been fired. Rapid detection of the end stop is used in powered surgical staplers to prevent damage to the device. During a surgical procedure, the stapler may detect an end stop of the end-effector assembly by measuring various operating parameters of the motor (e.g., torque or current). However, this approach relies on complicated software algorithms, which are costly to develop and implement. Further, if the end stop is not properly detected there is a high probability of the various moving components colliding upon reaching the end stop while the motor continues to operate, potentially resulting damage to the device. In addition to potentially damaging the device, hitting mechanical limits can also cause a twitch or unwanted jaw movement to develop within the loading unit, which can negatively affect accuracy and efficiency of the device when firing and can cause incremental damage over time.

Accordingly, a need exists for a low-cost electromechanical stapler capable of avoiding the negative effects of reaching mechanical limits, without the need of any costly software algorithms based on torque or motor current.

SUMMARY

The present disclosure provides a surgical powered stapler having a user-settable end stop distance that configures a motor actuating a stapler end effector to move for a predetermined distance associated with the user-selectable distance setting.

According to one embodiment of the present disclosure, a surgical stapler is disclosed. The surgical stapler includes a loading unit having: a staple cartridge having a cartridge distance and a plurality of staples and an anvil to form the plurality of staples upon firing. The surgical stapler also includes a shaft assembly coupled to the load unit. The shaft assembly includes a drive shaft longitudinally movable within the shaft assembly and configured to actuate the loading unit. The surgical stapler further includes a handle assembly having a power source and a motor coupled to the power source and configured to move the drive shaft longitudinally. The handle assembly also includes a distance setting interface including a plurality of switches each of which corresponds to a travel distance that the motor moves the drive shaft, the travel distance corresponding to the cartridge distance.

According to one aspect of the above embodiment, the distance setting interface includes a slide toggle configured to move within a slit defined in a housing of the handle assembly. The slide toggle is configured to engage each of the plurality of switches.

According to another aspect of the above embodiment, each switch of the plurality of switches includes a light source that is activated in response to engagement of a corresponding switch. Each switch of the plurality of switches is a latchable push-button switch movable from an unlatched state to a latched state upon actuation. The surgical stapler also includes a controller coupled to the distance setting interface and configured to reset the latched state of an actuated switch. A first switch of the plurality of switches is configured to operate the motor in a first mode. A second switch of the plurality of switches is configured to operate the motor in a second mode. During the first mode the motor is configured to move the drive shaft longitudinally until a mechanical limit is reached. During the second mode the motor is configured to move the drive shaft longitudinally until the travel distance is reached.

According to a further aspect of the above embodiment, a method for controlling a surgical stapler is disclosed. The method includes coupling a loading unit to a shaft assembly, the loading unit including a staple cartridge having a cartridge distance and a plurality of staples and an anvil to form the plurality of staples upon firing. The method also includes activating one switch of a plurality of switches disposed on a handle assembly and setting a travel distance corresponding to the cartridge distance in response to activating of the switch. The method further includes activating a motor disposed within the handle assembly to move a drive shaft longitudinally the travel distance to actuate the loading unit.

According to one aspect of the above embodiment, setting the travel distance includes moving a slide toggle configured to move within a slit defined in a housing of the handle assembly. The slide toggle is configured to engage each of the plurality of switches. The method further includes activating a light source associated with an activated switch.

According to another aspect of the above embodiment, each switch of the plurality of switches is a latchable push-button switch movable from an unlatched state to a latched state upon actuation. The method further includes resetting the latched state of an actuated switch. The method also includes activating a first switch of the plurality of switches to operate the motor in a first mode and activating a second switch of the plurality of switches to operate the motor in a second mode. The method further includes moving the drive shaft longitudinally until a mechanical limit is reached during the first mode and moving the drive shaft longitudinally until the travel distance is reached during the second mode.

BRIEF DESCRIPTION OF THE DRAWINGS

Various aspects of the disclosed surgical stapling device including proactive end stop selection mechanisms are described herein below with reference to the drawings, wherein.

DETAILED DESCRIPTION

Figure 1:
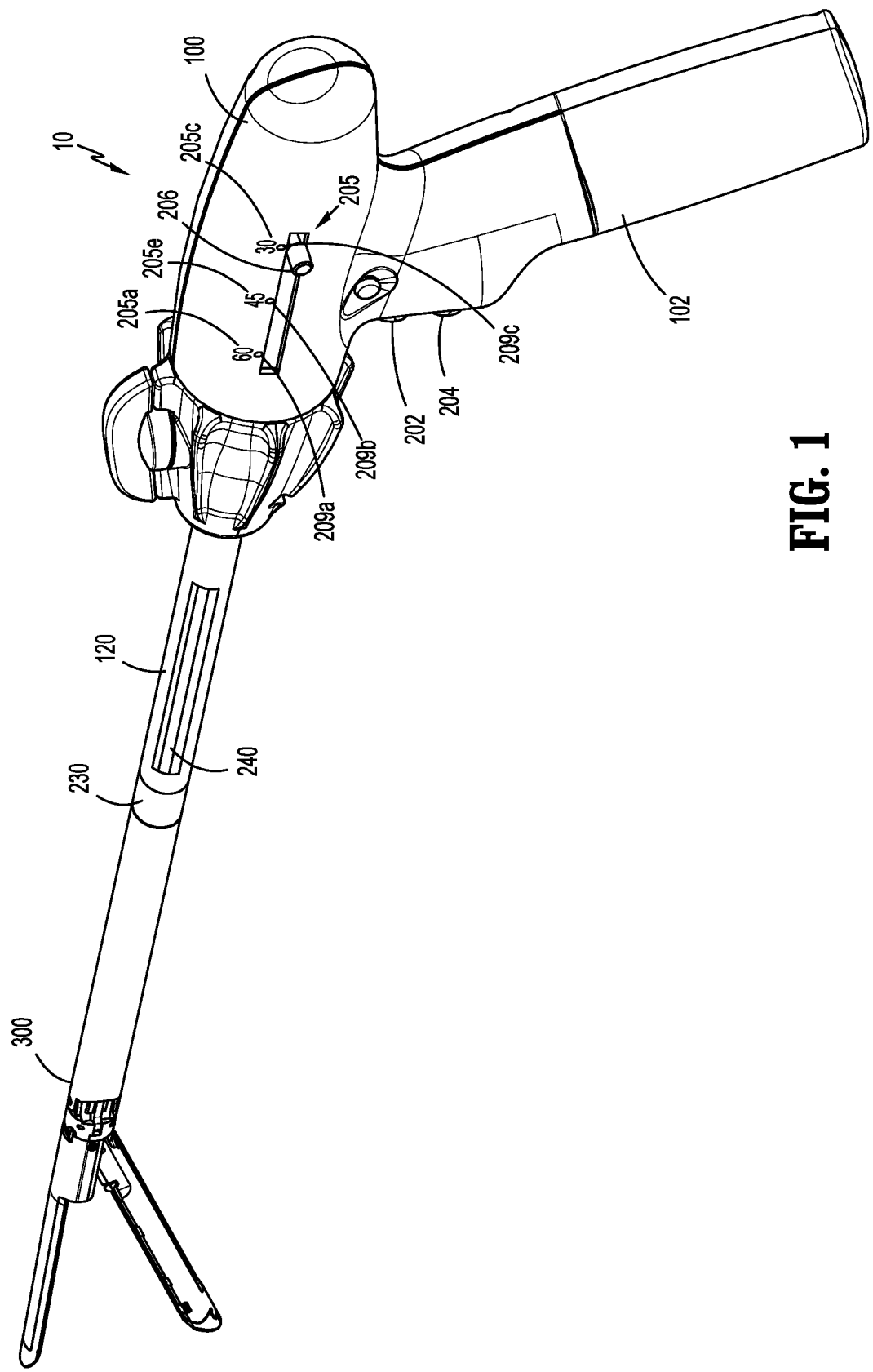
FIG. 1 is a perspective view of a powered surgical instrument according to an embodiment of the present disclosure.

The disclosed powered surgical staplers are described in detail with reference to the drawings in which like reference numerals designate identical or corresponding elements in each of the several views. However, it is to be understood that the aspects of the disclosure described herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during usage of the device in a customary manner, while the term "distal" is used generally to refer to that portion of the device that is farther from the clinician during usage of the device in a customary manner. In addition, the term "endoscopic" is used generally to refer to endoscopic, laparoscopic, arthroscopic, and/or any other procedure conducted through small diameter incision or cannula. Further, the term "clinician" is used generally to refer to medical personnel including doctors, nurses, and support personnel.

The systems described herein may utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

Referring initially to FIG. 1, an electromechanical, hand-held, powered surgical stapler, in accordance with aspects of the disclosure of the disclosure is shown and generally designated 10. Powered surgical stapler 10 includes a handle assembly 100 that is configured for selective attachment to of a plurality of different loading units 300 via a shaft assembly 120, that are each configured for actuation and manipulation by the handle assembly 100. The shaft assembly 120 includes a distal coupling 230 configured to connect to the loading unit 300 and houses a drive shaft 240. The drive shaft 240 is movable longitudinally within the shaft assembly 120.

The handle assembly 100 may be configured for selective connection with the shaft assembly 200, and, in turn, shaft assembly 120 is configured for selective connection with the loading unit 300. Handle assembly 100 includes a handle housing 102 housing various components described below with respect to FIG. 4, such as a motor, a drive shaft, and/or gear component configured to actuate the loading unit 300.

Figure 2:
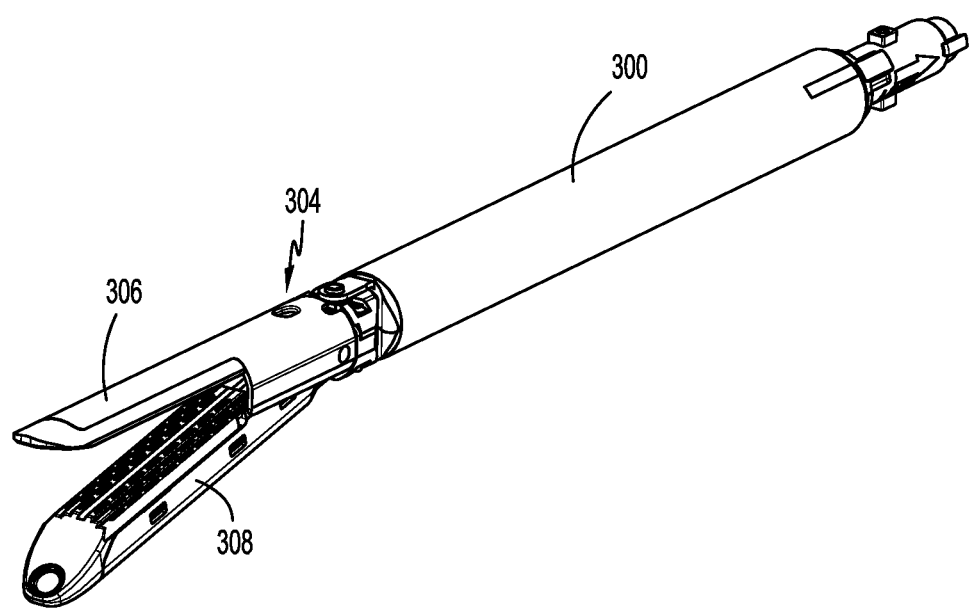
FIG. 2 is a perspective view of a loading unit for use with the powered surgical stapler of FIG. 1 according to an embodiment of the present disclosure.
Figure 3:
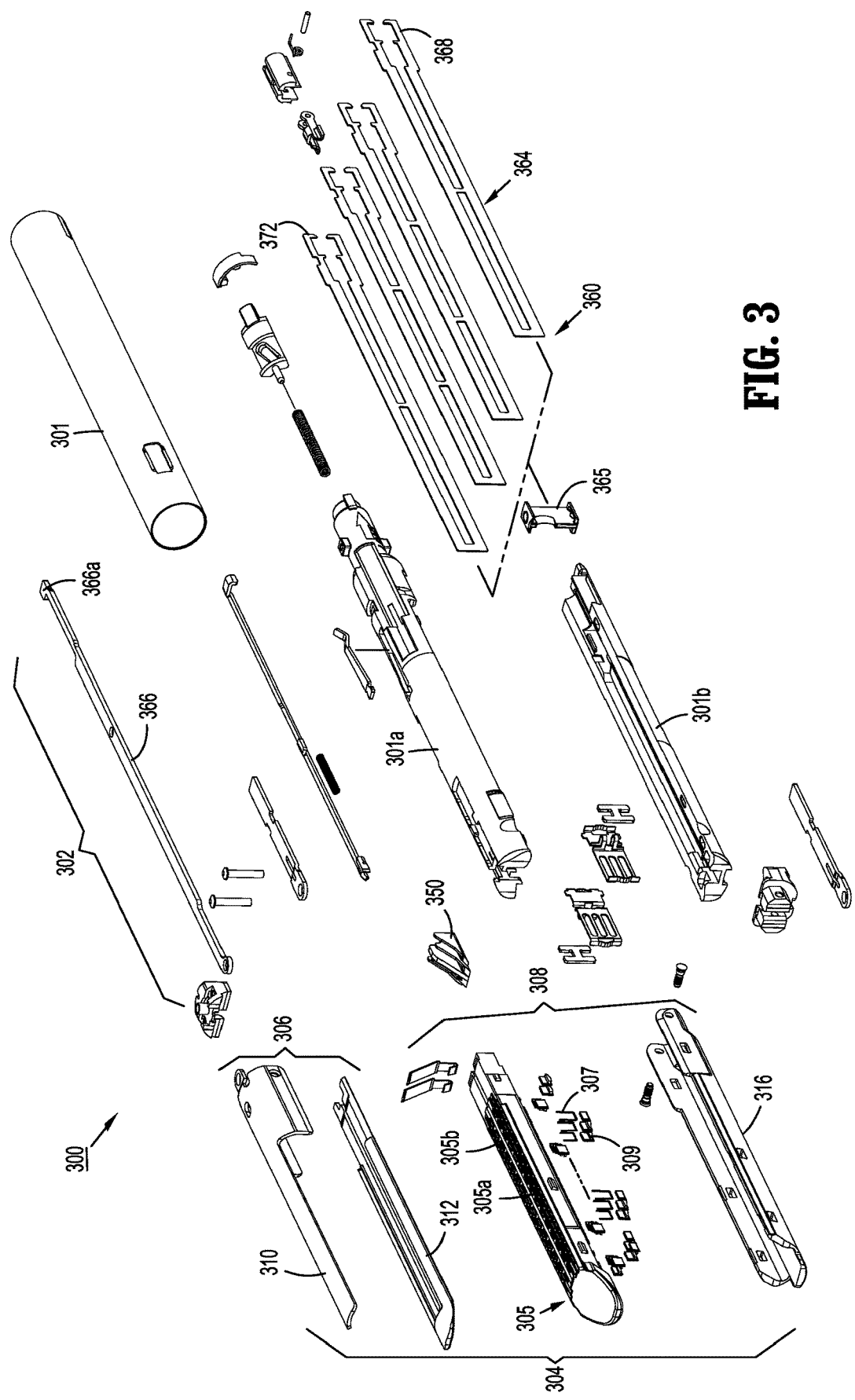
FIG. 3 is a perspective, exploded view of the loading unit of FIG. 2 according to an embodiment of the present disclosure.

With reference to FIGS. 2 and 3, the loading unit 300 includes an end effector 304 having an anvil assembly 306 and a cartridge assembly 308. The drive assembly 360 of loading unit 300 includes a flexible drive shaft 364 having a distal end which is secured to a drive beam 365, and a proximal engagement section 368, which is configured to couple to the drive shaft 240 (FIG. 1) of shaft assembly 120 when loading unit 300 is attached to distal coupling 230 of shaft assembly 120.

When drive assembly 360 is advanced distally within the loading unit 300, an upper beam of drive beam 365 moves within a channel defined between anvil plate 312 and anvil cover 310 and a lower beam moves within a channel of the staple cartridge 305 and over the exterior surface of carrier 316 to close end effector 304 and fire staples therefrom.

Proximal body portion 302 of loading unit 300 includes a sheath or outer tube 301 enclosing an upper housing portion 301a and a lower housing portion 301b. The housing portions 301a and 301b enclose an articulation link 366 having a hooked proximal end 366a which extends from a proximal end of loading unit 300. Hooked proximal end 366a of articulation link 366 engages a coupling hook (not shown) of shaft assembly 120 when loading unit 300 is secured to distal housing 232 of shaft assembly 120. When drive bar (not shown) of shaft assembly 120 is advanced or retracted as described above, articulation link 366 of loading unit 300 is advanced or retracted within loading unit 300 to pivot end effector 304 in relation to a distal end of proximal body portion 302.

The cartridge assembly 308 of end effector 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of powered surgical stapler 10, drive assembly 360 abuts an actuation sled 350 and pushes actuation sled 350 through cartridge 305. As the actuation sled moves through cartridge 305, cam wedges of the actuation sled 350 sequentially engage staple pushers 309 to move staple pushers 309 vertically within staple retention slots 305b and sequentially eject the staples 307 therefrom for formation against anvil plate 312.

Figure 4:
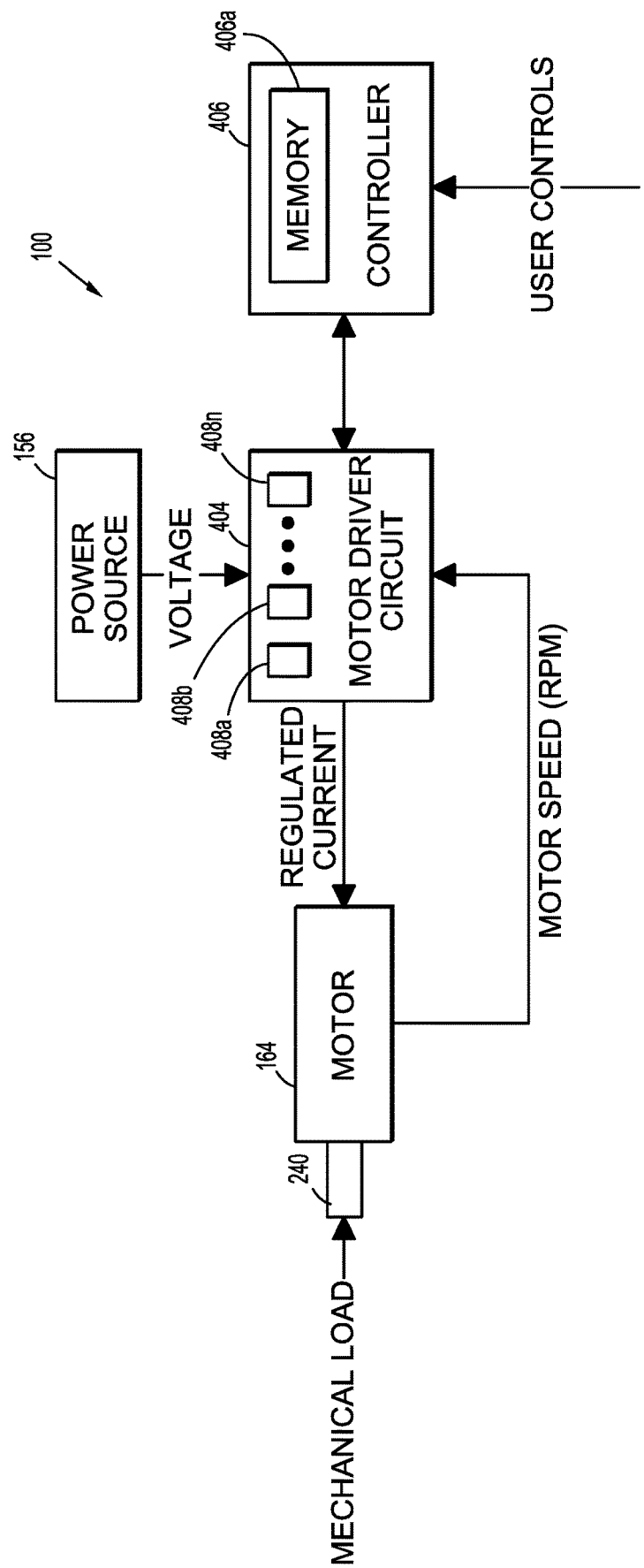
FIG. 4 is a schematic diagram of the surgical instrument of FIG. 1 according to an embodiment of the present disclosure.

With reference to FIG. 4, the powered surgical stapler 10 includes a motor 164, which may be any electrical motor configured to actuate one or more drive shafts 240. The motor 164 is coupled to a battery 156, which may be a DC battery (e.g., rechargeable lead-based, nickel-based, lithium-ion based, battery etc.), an AC/DC transformer, or any other power source suitable for providing electrical energy to the motor 164.

The battery 156 and the motor 164 are coupled to a motor driver circuit 404 disposed on the circuit board 154 which controls the operation of the motor 164 including the flow of electrical energy from the battery 156 to the motor 164. The driver circuit 404 may include a plurality of sensors 408a, 408b, . . . 408n configured to measure operational states of the motor 164 and the battery 156. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 156. The sensors 408a-408n may also measure rotational speed as revolutions per minute (RPM), torque, temperature, current draw, and other operational properties of the motor 164. RPM may be determined by measuring the rotation of the motor 164. Position of the drive shaft 240 may be determined by using various linear sensors disposed in or in proximity to the shafts or extrapolated from the RPM measurements. In embodiments, torque may be calculated based on the regulated current draw of the motor 164 at a constant RPM. In further embodiments, the driver circuit 404 and/or the controller 406 may measure time and process the above-described values as a function thereof, including integration and/or differentiation, e.g., to determine the change in the measured values and the like.

The driver circuit 404 is also coupled to a controller 406, which may be any suitable logic control circuit adapted to perform the calculations and/or operate according to a set of instructions described in further detail below. The controller 406 may include a central processing unit operably connected to a memory which may include transitory type memory (e.g., RAM) and/or non-transitory type memory (e.g., flash media, disk media, etc.). The controller 406 includes a plurality of inputs and outputs for interfacing with the driver circuit 404. In particular, the controller 406 receives measured sensor signals from the driver circuit 404 regarding operational status of the motor 164 and the battery 156 and, in turn, outputs control signals to the driver circuit 404 to control the operation of the motor 164 based on the sensor readings and specific algorithm instructions, which are discussed in more detail below. The controller 406 is also configured to accept a plurality of user inputs from a user interface (e.g., buttons 202 and 204, distance setting interface 205, etc., which are coupled to the controller 406).

With reference to FIG. 1, the powered surgical stapler 10 includes a pair of buttons 202 and 204 configured to activate the motor 164 to operate the drive shaft 240 longitudinally in a distal and proximal directions, respectively. As the button 202 is pressed, the motor 164 is operated in a first direction, e.g., rotated clockwise, drive shaft 240 is moved distally, the drive assembly 360 of the loading unit 300 is also moved in a distal direction along with the drive beam 365. This in turn, moves the anvil assembly 306 toward the cartridge assembly 308 and simultaneously ejects staples 307 to clamp, staple, and cut tissue clamped between the anvil assembly 306 toward the cartridge assembly 308. Pressing the button 204 reverses the motor 164 and the motor 164 is operated in a second direction, e.g., rotated counterclockwise. The drive shaft 240 is withdrawn, and is moved proximally, which retracts the drive assembly 360 and moves the anvil assembly 306 away from the cartridge assembly 308.

The end effector 304 may be of any suitable size, such as 30 mm, 45 mm, and 60 mm, and the setting interface 205 includes options for configuring the distance for each of the end effectors 304 that are usable with the powered surgical stapler 10. With reference to FIG. 1, the powered surgical stapler 10 includes the distance setting interface 205 having a slide toggle 206 and a plurality of switches 205a, 205b, 205c, each of which is associated with a predetermined travel distance that the drive beam 365 is advanced during firing, namely, 30 mm, 45 mm, and 60 mm. The switches 205a, 205b, 205c may be button switches or limit switches, such that as a slide toggle 206 is moved within a slit 210, the slide toggle 206 actuates the switches 205a, 205b, 205c corresponding to the desired distance. The slit 210 is defined within the housing 102 of the handle assembly 100. Each of the switches 208a, 208b, 208b generates a distance signal corresponding to the distance. The desired distance signal is communicated to controller 406 or directly to the motor 164, which is then set to rotate a corresponding number of rotations to achieve the selected distance based on the distance signal. The number of turns is preprogrammed into the controller 406 or into the driver circuit 404, thus obviating the need for relying on feedback from the sensors 408a-408n to control the movement of the drive assembly 360.

Once the loading unit 300 is coupled to the shaft assembly 120, the user then inputs the travel distance that corresponds to the size of the end effector 304 by moving the slide toggle 206 to engage the corresponding switch 205a, 205b, 205c. If an incorrect switch is pressed, the user may move the toggle to the desired position. The position of the slide toggle 206 may be indicated by a light 209a, 209b, 209c, corresponding to each of the switches 205a, 205b, 205c. Once the distance is set, the user presses the button 202, the motor 164 is operated in a first direction, e.g., rotated clockwise, for a predetermined number of turns to achieve the selected distance. The motor 164 actuates the end effector 304 to clamp, staple, and cut tissue clamped between the anvil assembly 306 toward the cartridge assembly 308. Thereafter, the user presses the button 204, which operates the motor 164 in a reverse direction for the same number of turns to retract the drive assembly 360 and moves the anvil assembly 306 away from the cartridge assembly 308.

Figure 5:
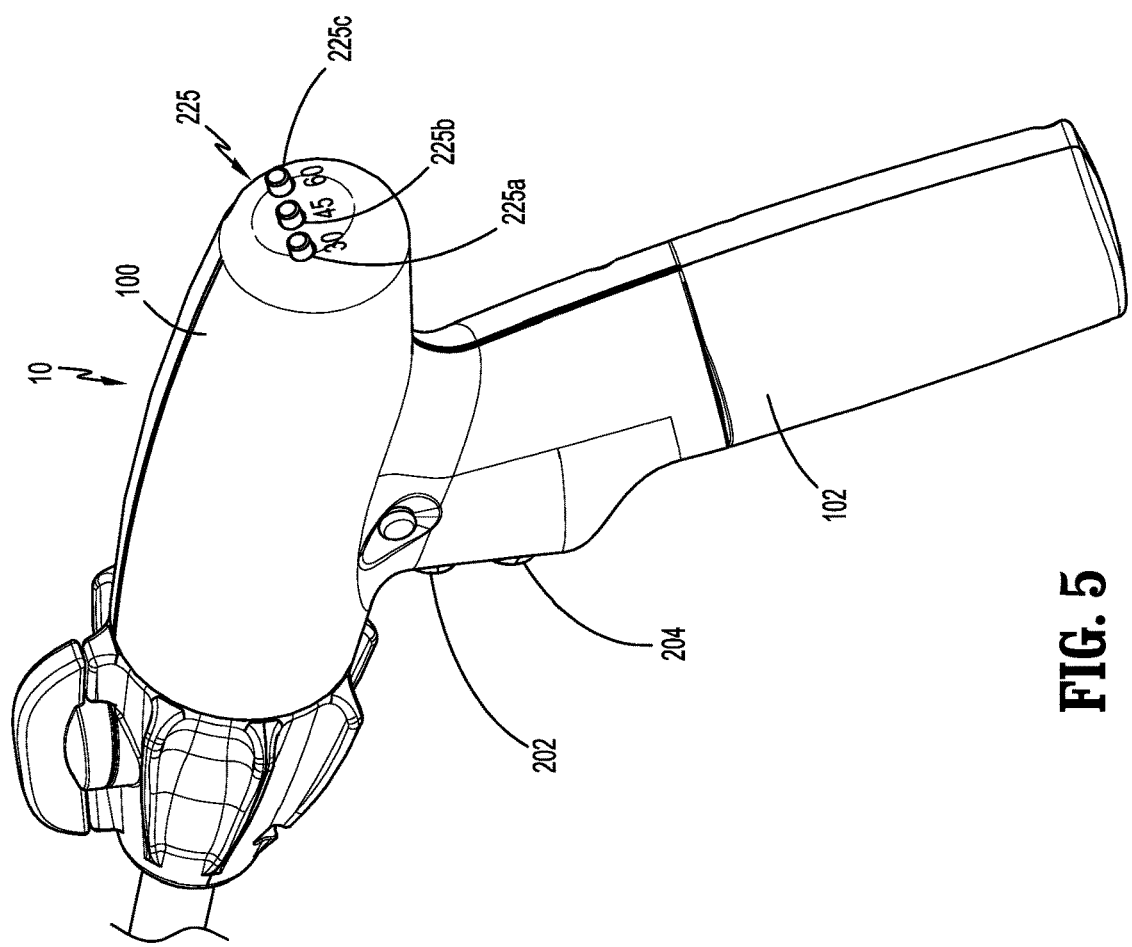
FIG. 5 is a perspective view of a handle assembly of the surgical instrument of FIG. 1 according to another embodiment of the present disclosure.

Another embodiment of a distance setting interface 225 is shown in FIG. 5 in which each of the switches 225a, 225b, 225c, are push-button switches which are manually toggled by the user rather than by the slide toggle 206. The switches 225a, 225b, 225c may incorporate a light within the button to indicate their toggle state. In further embodiments, the switches 225a, 225b, 225c may be latch switches, which remain in a depressed state rafter being toggled. After being toggled, the user then operates the powered surgical stapler 10 by pressing the buttons 202 and 204 to close and open the end effector 304. After the loading unit 300 is removed, the toggled switch of the switches 225a, 225b, 225c is reset.

Figure 6:
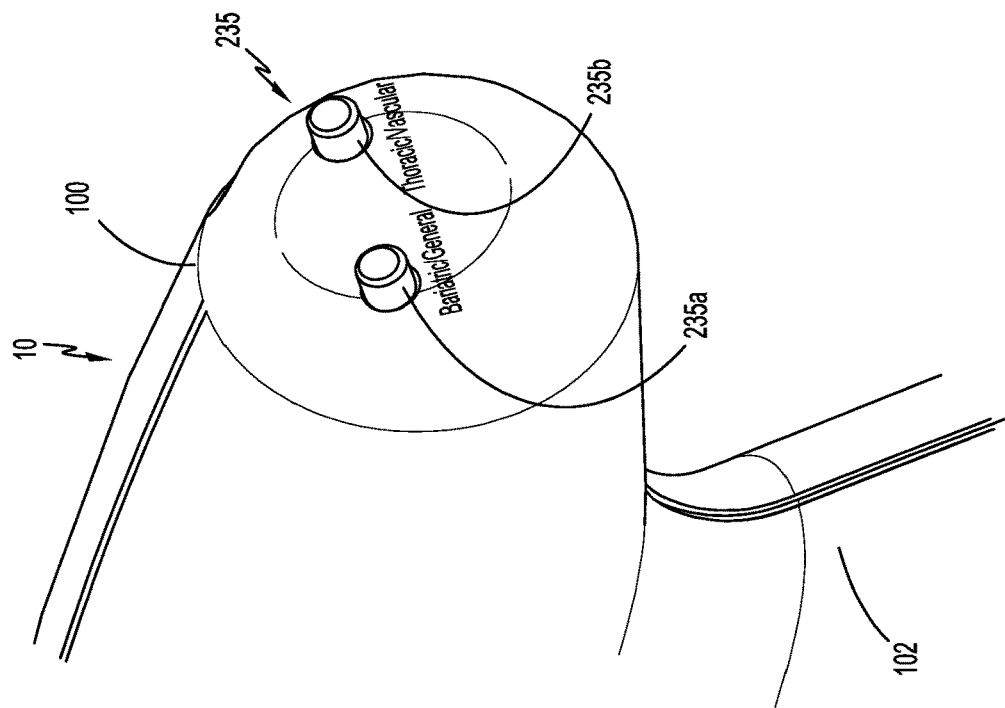
FIG. 6 is a perspective view of a handle assembly of the surgical instrument of FIG. 1 according to a further embodiment of the present disclosure.

Another embodiment of a distance setting interface 235 is shown in FIG. 6. The distance setting interface 235 is similar to the distance setting interface 225 and includes push-button toggle switches 235a and 235b, each associated with a different travel distance setting for the motor 164. The switches 235a and 235b may also include light indicators and may be latchable, resettable switches as described above. In embodiments, the switch 235a activates the motor 164 to operate in a first mode, useful for bariatric or general use, during which the motor 164 is operated continuously until the motor 164 reaches a mechanical limit and stalls. The switch 235b activates the motor 164 to operate in a second mode, during which the motor 164 is operated for a predetermined distance, similar to the distance modes of the distance setting interfaces 205 and 225.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapler comprising:
a loading unit including:
a staple cartridge having a cartridge distance and a plurality of staples; and
an anvil to form the plurality of staples upon firing;
a shaft assembly coupled to the load unit, the shaft assembly including a drive shaft longitudinally movable within the shaft assembly and configured to actuate the loading unit; and
a handle assembly including:
a power source;
a motor coupled to the power source and configured to move the drive shaft longitudinally; and
a distance setting interface including:
a plurality of switches each of which corresponds to a travel distance that the motor moves the drive shaft, the travel distance corresponding to the cartridge distance; and
a slide toggle configured to move within a slit defined in a housing of the handle assembly.

2. The surgical stapler according to claim 1, wherein the slide toggle is configured to engage each of the plurality of switches.

3. The surgical stapler according to claim 1, wherein each switch of the plurality of switches includes a light source that is activated in response to engagement of a corresponding switch.

4. The surgical stapler according to claim 1, wherein each switch of the plurality of switches is a latchable push-button switch movable from an unlatched state to a latched state upon actuation.

5. The surgical stapler according to claim 4, further comprising a controller coupled to the distance setting interface and configured to reset the latched state of an actuated switch.

6. The surgical stapler according to claim 5, wherein a first switch of the plurality of switches is configured to operate the motor in a first mode.

7. The surgical stapler according to claim 6, wherein a second switch of the plurality of switches is configured to operate the motor in a second mode.

8. The surgical stapler according to claim 7, wherein during the first mode the motor is configured to move the drive shaft longitudinally until a mechanical limit is reached.

9. The surgical stapler according to claim 8, wherein during the second mode the motor is configured to move the drive shaft longitudinally until the travel distance is reached.

10. A method for controlling a surgical stapler including a loading unit coupled to a shaft assembly, the loading unit including a staple cartridge having a cartridge distance and a plurality of staples and an anvil to form the plurality of staples upon firing, the method comprising:
receiving a signal in response to activation of one switch of a plurality of switches disposed on a handle assembly wherein the switch is activated by a slide toggle configured to move within a slit defined in a housing of the handle assembly;
setting a travel distance corresponding to the cartridge distance in response to activating of the switch; and
activating a motor disposed within the handle assembly to move a drive shaft longitudinally the travel distance to actuate the loading unit.

11. The method according to claim 10, wherein the slide toggle is configured to engage each of the plurality of switches.

12. The method according to claim 10, further comprising activating a light source associated with an activated switch.

13. The method according to claim 10, wherein each switch of the plurality of switches is a latchable push-button switch movable from an unlatched state to a latched state upon actuation.

14. The method according to claim 13, further comprising resetting the latched state of an actuated switch.

15. The method according to claim 10, activating a first switch of the plurality of switches to operate the motor in a first mode.

16. The method according to claim 15, activating a second switch of the plurality of switches to operate the motor in a second mode.

17. The method according to claim 16, further comprising moving the drive shaft longitudinally until a mechanical limit is reached during the first mode.

18. The method according to claim 16, further comprising moving the drive shaft longitudinally until the travel distance is reached during the second mode.

* * * * *